United States Patent
Hernanta (10) Patent No.: US 9,082,447 B1
(45) Date of Patent: Jul. 14, 2015

(54) DETERMINING STORAGE MEDIA SUBSTRATE MATERIAL TYPE

(71) Applicant: WD Media, LLC, San Jose, CA (US)

(72) Inventor: Hernanta, Singapore (SG)

(73) Assignee: WD Media, LLC, San Jose, CA (US)

( * ) Notice: Subject to any disclaimer, the term of this patent is extended or adjusted under 35 U.S.C. 154(b) by 0 days.

(21) Appl. No.: 14/492,292

(22) Filed: Sep. 22, 2014

(51) Int. Cl.
- *G11B 5/84* (2006.01)
- *G11B 19/10* (2006.01)
- *G01N 27/02* (2006.01)
- *G11B 19/12* (2006.01)

(52) U.S. Cl.
CPC ............... *G11B 19/10* (2013.01); *G01N 27/02* (2013.01); *G11B 5/8404* (2013.01); *G11B 19/12* (2013.01); *G11B 2019/121* (2013.01)

(58) Field of Classification Search
None
See application file for complete search history.

(56) References Cited

U.S. PATENT DOCUMENTS

| | | |
|---|---|---|
| 5,289,451 A | 2/1994 | Ashinuma et al. |
| 5,700,127 A | 12/1997 | Harada et al. |
| 6,013,161 A | 1/2000 | Chen et al. |
| 6,063,248 A | 5/2000 | Bourez et al. |
| 6,068,891 A | 5/2000 | O'Dell et al. |
| 6,086,730 A | 7/2000 | Liu et al. |
| 6,099,981 A | 8/2000 | Nishimori |
| 6,103,404 A | 8/2000 | Ross et al. |
| 6,117,499 A | 9/2000 | Wong et al. |
| 6,136,403 A | 10/2000 | Prabhakara et al. |
| 6,143,375 A | 11/2000 | Ross et al. |
| 6,145,849 A | 11/2000 | Bae et al. |
| 6,146,737 A | 11/2000 | Malhotra et al. |
| 6,149,696 A | 11/2000 | Jia |
| 6,150,015 A | 11/2000 | Bertero et al. |
| 6,156,404 A | 12/2000 | Ross et al. |
| 6,159,076 A | 12/2000 | Sun et al. |
| 6,164,118 A | 12/2000 | Suzuki et al. |
| 6,200,441 B1 | 3/2001 | Gornicki et al. |
| 6,204,995 B1 | 3/2001 | Hokkyo et al. |
| 6,206,765 B1 | 3/2001 | Sanders et al. |
| 6,210,819 B1 | 4/2001 | Lal et al. |
| 6,216,709 B1 | 4/2001 | Fung et al. |
| 6,221,119 B1 | 4/2001 | Homola |
| 6,248,395 B1 | 6/2001 | Homola et al. |
| 6,261,681 B1 | 7/2001 | Suekane et al. |
| 6,270,885 B1 | 8/2001 | Hokkyo et al. |
| 6,273,261 B1 | 8/2001 | Hosoi |
| 6,274,063 B1 | 8/2001 | Li et al. |
| 6,283,838 B1 | 9/2001 | Blake et al. |
| 6,286,688 B1 | 9/2001 | Mimken et al. |
| 6,287,429 B1 | 9/2001 | Moroishi et al. |
| 6,290,573 B1 | 9/2001 | Suzuki |
| 6,299,947 B1 | 10/2001 | Suzuki et al. |
| 6,303,217 B1 | 10/2001 | Malhotra et al. |
| 6,309,765 B1 | 10/2001 | Suekane et al. |
| 6,358,636 B1 | 3/2002 | Yang et al. |
| 6,362,452 B1 | 3/2002 | Suzuki et al. |
| 6,363,599 B1 | 4/2002 | Bajorek |
| 6,365,012 B1 | 4/2002 | Sato et al. |
| 6,381,090 B1 | 4/2002 | Suzuki et al. |
| 6,381,092 B1 | 4/2002 | Suzuki |

(Continued)

*Primary Examiner* — Wayne Young
*Assistant Examiner* — Brian Butcher (57) ABSTRACT

A method, system, and computer program product are disclosed for determining a material type of storage media substrates. The method includes using a first sensor to detect an object that indicates the presence of at least one storage media substrate, and using an inductive sensor to determine whether the at least one storage media substrate is of a metallic type.

21 Claims, 5 Drawing Sheets

(56) References Cited

U.S. PATENT DOCUMENTS

| | | | |
|---|---|---|---|
| 6,387,483 B1 | 5/2002 | Hokkyo et al. |
| 6,391,213 B1 | 5/2002 | Homola |
| 6,395,349 B1 | 5/2002 | Salamon |
| 6,403,919 B1 | 6/2002 | Salamon |
| 6,408,677 B1 | 6/2002 | Suzuki |
| 6,426,157 B1 | 7/2002 | Hokkyo et al. |
| 6,429,984 B1 | 8/2002 | Alex |
| 6,482,330 B1 | 11/2002 | Bajorek |
| 6,482,505 B1 | 11/2002 | Bertero et al. |
| 6,500,567 B1 | 12/2002 | Bertero et al. |
| 6,528,124 B1 | 3/2003 | Nguyen |
| 6,548,821 B1 | 4/2003 | Treves et al. |
| 6,552,871 B2 | 4/2003 | Suzuki et al. |
| 6,565,719 B1 | 5/2003 | Lairson et al. |
| 6,566,674 B1 | 5/2003 | Treves et al. |
| 6,571,806 B2 | 6/2003 | Rosano et al. |
| 6,628,466 B2 | 9/2003 | Alex |
| 6,664,503 B1 | 12/2003 | Hsieh et al. |
| 6,670,055 B2 | 12/2003 | Tomiyasu et al. |
| 6,682,807 B2 | 1/2004 | Lairson et al. |
| 6,683,754 B2 | 1/2004 | Suzuki et al. |
| 6,730,420 B1 | 5/2004 | Bertero et al. |
| 6,743,528 B2 | 6/2004 | Suekane et al. |
| 6,745,901 B2 | 6/2004 | Chen et al. |
| 6,759,138 B2 | 7/2004 | Tomiyasu et al. |
| 6,775,918 B2 | 8/2004 | Tseng et al. |
| 6,778,353 B1 | 8/2004 | Harper |
| 6,781,205 B1 | 8/2004 | Levit et al. |
| 6,795,274 B1 | 9/2004 | Hsieh et al. |
| 6,855,232 B2 | 2/2005 | Jairson et al. |
| 6,857,937 B2 | 2/2005 | Bajorek |
| 6,874,638 B2 | 4/2005 | Iijima et al. |
| 6,893,748 B2 | 5/2005 | Bertero et al. |
| 6,899,959 B2 | 5/2005 | Bertero et al. |
| 6,916,558 B2 | 7/2005 | Umezawa et al. |
| 6,939,120 B1 | 9/2005 | Harper |
| 6,946,191 B2 | 9/2005 | Morikawa et al. |
| 6,967,798 B2 | 11/2005 | Homola et al. |
| 6,972,135 B2 | 12/2005 | Homola |
| 7,004,827 B1 | 2/2006 | Suzuki et al. |
| 7,006,323 B1 | 2/2006 | Suzuki |
| 7,016,154 B2 | 3/2006 | Nishihira |
| 7,019,924 B2 | 3/2006 | McNeil et al. |
| 7,027,894 B2 | 4/2006 | Kretz et al. |
| 7,042,558 B2 | 5/2006 | Sarfaty et al. |
| 7,045,215 B2 | 5/2006 | Shimokawa |
| 7,057,386 B1 | 6/2006 | Franklin |
| 7,070,870 B2 | 7/2006 | Bertero et al. |
| 7,090,934 B2 | 8/2006 | Hokkyo et al. |
| 7,099,112 B1 | 8/2006 | Harper |
| 7,105,241 B2 | 9/2006 | Shimokawa et al. |
| 7,119,990 B2 | 10/2006 | Bajorek et al. |
| 7,147,790 B2 | 12/2006 | Wachenschwanz et al. |
| 7,161,753 B2 | 1/2007 | Wachenschwanz et al. |
| 7,166,319 B2 | 1/2007 | Ishiyama |
| 7,166,374 B2 | 1/2007 | Suekane et al. |
| 7,169,487 B2 | 1/2007 | Kawai et al. |
| 7,174,775 B2 | 2/2007 | Ishiyama |
| 7,179,549 B2 | 2/2007 | Malhotra et al. |
| 7,184,139 B2 | 2/2007 | Treves et al. |
| 7,195,808 B2 | 3/2007 | Yi |
| 7,196,860 B2 | 3/2007 | Alex |
| 7,199,977 B2 | 4/2007 | Suzuki et al. |
| 7,208,236 B2 | 4/2007 | Morikawa et al. |
| 7,220,500 B1 | 5/2007 | Tomiyasu et al. |
| 7,229,266 B2 | 6/2007 | Harper |
| 7,239,970 B2 | 7/2007 | Treves et al. |
| 7,252,897 B2 | 8/2007 | Shimokawa et al. |
| 7,277,254 B2 | 10/2007 | Shimokawa et al. |
| 7,281,920 B2 | 10/2007 | Homola et al. |
| 7,292,329 B2 | 11/2007 | Treves et al. |
| 7,301,726 B1 | 11/2007 | Suzuki |
| 7,302,148 B2 | 11/2007 | Treves et al. |
| 7,305,119 B2 | 12/2007 | Treves et al. |
| 7,314,404 B2 | 1/2008 | Singh et al. |
| 7,320,584 B1 | 1/2008 | Harper et al. |
| 7,329,114 B2 | 2/2008 | Harper et al. |
| 7,375,362 B2 | 5/2008 | Treves et al. |
| 7,420,886 B2 | 9/2008 | Tomiyasu et al. |
| 7,425,719 B2 | 9/2008 | Treves et al. |
| 7,471,484 B2 | 12/2008 | Wachenschwanz et al. |
| 7,498,062 B2 | 3/2009 | Calcaterra et al. |
| 7,531,485 B2 | 5/2009 | Hara et al. |
| 7,537,846 B2 | 5/2009 | Ishiyama et al. |
| 7,549,209 B2 | 6/2009 | Wachenschwanz et al. |
| 7,569,490 B2 | 8/2009 | Staud |
| 7,597,792 B2 | 10/2009 | Homola et al. |
| 7,597,973 B2 | 10/2009 | Ishiyama |
| 7,608,193 B2 | 10/2009 | Wachenschwanz et al. |
| 7,632,087 B2 | 12/2009 | Homola |
| 7,656,615 B2 | 2/2010 | Wachenschwanz et al. |
| 7,682,546 B2 | 3/2010 | Harper |
| 7,684,152 B2 | 3/2010 | Suzuki et al. |
| 7,686,606 B2 | 3/2010 | Harper et al. |
| 7,686,991 B2 | 3/2010 | Harper |
| 7,695,833 B2 | 4/2010 | Ishiyama |
| 7,710,684 B2 | 5/2010 | Hashimoto |
| 7,722,968 B2 | 5/2010 | Ishiyama |
| 7,733,605 B2 | 6/2010 | Suzuki et al. |
| 7,736,768 B2 | 6/2010 | Ishiyama |
| 7,755,861 B1 | 7/2010 | Li et al. |
| 7,758,732 B1 | 7/2010 | Calcaterra et al. |
| 7,833,639 B2 | 11/2010 | Sonobe et al. |
| 7,833,641 B2 | 11/2010 | Tomiyasu et al. |
| 7,855,549 B2 | 12/2010 | Renken et al. |
| 7,894,923 B2 | 2/2011 | Koshti et al. |
| 7,910,159 B2 | 3/2011 | Jung |
| 7,911,736 B2 | 3/2011 | Bajorek |
| 7,924,519 B2 | 4/2011 | Lambert |
| 7,944,165 B1 | 5/2011 | O'Dell |
| 7,944,643 B1 | 5/2011 | Jiang et al. |
| 7,955,723 B2 | 6/2011 | Umezawa et al. |
| 7,983,003 B2 | 7/2011 | Sonobe et al. |
| 7,993,497 B2 | 8/2011 | Moroishi et al. |
| 7,993,765 B2 | 8/2011 | Kim et al. |
| 7,998,912 B2 | 8/2011 | Chen et al. |
| 8,002,901 B1 | 8/2011 | Chen et al. |
| 8,003,237 B2 | 8/2011 | Sonobe et al. |
| 8,012,920 B2 | 9/2011 | Shimokawa |
| 8,038,863 B2 | 10/2011 | Homola |
| 8,057,926 B2 | 11/2011 | Ayama et al. |
| 8,062,778 B2 | 11/2011 | Suzuki et al. |
| 8,064,156 B1 | 11/2011 | Suzuki et al. |
| 8,076,013 B2 | 12/2011 | Sonobe et al. |
| 8,092,931 B2 | 1/2012 | Ishiyama et al. |
| 8,100,685 B1 | 1/2012 | Harper et al. |
| 8,101,054 B2 | 1/2012 | Chen et al. |
| 8,125,723 B1 | 2/2012 | Nichols et al. |
| 8,125,724 B1 | 2/2012 | Nichols et al. |
| 8,137,517 B1 | 3/2012 | Bourez |
| 8,142,916 B2 | 3/2012 | Umezawa et al. |
| 8,163,093 B1 | 4/2012 | Chen et al. |
| 8,171,949 B1 | 5/2012 | Lund et al. |
| 8,173,282 B1 | 5/2012 | Sun et al. |
| 8,178,480 B2 | 5/2012 | Hamakubo et al. |
| 8,206,789 B2 | 6/2012 | Suzuki |
| 8,218,260 B2 | 7/2012 | Iamratanakul et al. |
| 8,247,095 B2 | 8/2012 | Champion et al. |
| 8,257,783 B2 | 9/2012 | Suzuki et al. |
| 8,298,609 B1 | 10/2012 | Liew et al. |
| 8,298,689 B2 | 10/2012 | Sonobe et al. |
| 8,309,239 B2 | 11/2012 | Umezawa et al. |
| 8,316,668 B1 | 11/2012 | Chan et al. |
| 8,331,056 B2 | 12/2012 | O'Dell |
| 8,354,618 B1 | 1/2013 | Chen et al. |
| 8,367,228 B2 | 2/2013 | Sonobe et al. |
| 8,383,209 B2 | 2/2013 | Ayama |
| 8,394,243 B1 | 3/2013 | Jung et al. |
| 8,397,751 B1 | 3/2013 | Chan et al. |
| 8,399,809 B1 | 3/2013 | Bourez |
| 8,402,638 B1 | 3/2013 | Treves et al. |
| 8,404,056 B1 | 3/2013 | Chen et al. |
| 8,404,369 B2 | 3/2013 | Ruffini et al. |
| 8,404,370 B2 | 3/2013 | Sato et al. |

(56) References Cited

U.S. PATENT DOCUMENTS

| | | |
|---|---|---|
| 8,406,918 B2 | 3/2013 | Tan et al. |
| 8,414,966 B2 | 4/2013 | Yasumori et al. |
| 8,425,975 B2 | 4/2013 | Ishiyama |
| 8,431,257 B2 | 4/2013 | Kim et al. |
| 8,431,258 B2 | 4/2013 | Onoue et al. |
| 8,453,315 B2 | 6/2013 | Kajiwara et al. |
| 8,488,276 B1 | 7/2013 | Jung et al. |
| 8,491,800 B1 | 7/2013 | Dorsey |
| 8,492,009 B1 | 7/2013 | Homola et al. |
| 8,492,011 B2 | 7/2013 | Itoh et al. |
| 8,496,466 B1 | 7/2013 | Treves et al. |
| 8,517,364 B1 | 8/2013 | Crumley et al. |
| 8,517,657 B2 | 8/2013 | Chen et al. |
| 8,524,052 B1 | 9/2013 | Tan et al. |
| 8,530,065 B1 | 9/2013 | Chernyshov et al. |
| 8,546,000 B2 | 10/2013 | Umezawa |
| 8,551,253 B2 | 10/2013 | Na'im et al. |
| 8,551,627 B2 | 10/2013 | Shimada et al. |
| 8,556,566 B1 | 10/2013 | Suzuki et al. |
| 8,559,131 B2 | 10/2013 | Masuda et al. |
| 8,562,748 B1 | 10/2013 | Chen et al. |
| 8,565,050 B1 | 10/2013 | Bertero et al. |
| 8,570,844 B1 | 10/2013 | Yuan et al. |
| 8,580,410 B2 | 11/2013 | Onoue |
| 8,584,687 B1 | 11/2013 | Chen et al. |
| 8,591,709 B1 | 11/2013 | Lim et al. |
| 8,592,061 B2 | 11/2013 | Onoue et al. |
| 8,596,287 B1 | 12/2013 | Chen et al. |
| 8,597,723 B1 | 12/2013 | Jung et al. |
| 8,603,649 B2 | 12/2013 | Onoue |
| 8,603,650 B2 | 12/2013 | Sonobe et al. |
| 8,605,388 B2 | 12/2013 | Yasumori et al. |
| 8,605,555 B1 | 12/2013 | Chernyshov et al. |
| 8,608,147 B1 | 12/2013 | Yap et al. |
| 8,609,263 B1 | 12/2013 | Chernyshov et al. |
| 8,619,381 B2 | 12/2013 | Moser et al. |
| 8,623,528 B2 | 1/2014 | Umezawa et al. |
| 8,623,529 B2 | 1/2014 | Suzuki |
| 8,629,770 B2 | 1/2014 | Hummer et al. |
| 8,634,155 B2 | 1/2014 | Yasumori et al. |
| 8,657,644 B2 | 2/2014 | Tada et al. |
| 8,658,003 B1 | 2/2014 | Bourez |
| 8,658,292 B1 | 2/2014 | Mallary et al. |
| 8,665,541 B2 | 3/2014 | Saito |
| 8,668,953 B1 | 3/2014 | Buechel-Rimmel |
| 8,674,327 B1 | 3/2014 | Poon et al. |
| 8,685,214 B1 | 4/2014 | Moh et al. |
| 8,696,404 B2 | 4/2014 | Sun et al. |
| 8,711,499 B1 | 4/2014 | Desai et al. |
| 8,743,666 B1 | 6/2014 | Bertero et al. |
| 8,758,912 B2 | 6/2014 | Srinivasan et al. |
| 8,787,124 B1 | 7/2014 | Chernyshov et al. |
| 8,787,130 B1 | 7/2014 | Yuan et al. |
| 8,791,391 B2 | 7/2014 | Bourez |
| 8,795,765 B2 | 8/2014 | Koike et al. |
| 8,795,790 B2 | 8/2014 | Sonobe et al. |
| 8,795,857 B2 | 8/2014 | Ayama et al. |
| 8,800,322 B1 | 8/2014 | Chan et al. |
| 8,811,129 B1 | 8/2014 | Yuan et al. |
| 8,817,410 B1 | 8/2014 | Moser et al. |
| 2002/0060883 A1 | 5/2002 | Suzuki |
| 2003/0022024 A1 | 1/2003 | Wachenschwanz |
| 2004/0022387 A1 | 2/2004 | Weikle |
| 2004/0132301 A1 | 7/2004 | Harper et al. |
| 2004/0202793 A1 | 10/2004 | Harper et al. |
| 2004/0202865 A1 | 10/2004 | Homola et al. |
| 2004/0209123 A1 | 10/2004 | Bajorek et al. |
| 2004/0209470 A1 | 10/2004 | Bajorek |
| 2005/0036223 A1 | 2/2005 | Wachenschwanz et al. |
| 2005/0142990 A1 | 6/2005 | Homola |
| 2005/0150862 A1 | 7/2005 | Harper et al. |
| 2005/0151282 A1 | 7/2005 | Harper et al. |
| 2005/0151283 A1 | 7/2005 | Bajorek et al. |
| 2005/0151300 A1 | 7/2005 | Harper et al. |
| 2005/0155554 A1 | 7/2005 | Saito |
| 2005/0167867 A1 | 8/2005 | Bajorek et al. |
| 2005/0263401 A1 | 12/2005 | Olsen et al. |
| 2006/0147758 A1 | 7/2006 | Jung et al. |
| 2006/0181697 A1 | 8/2006 | Treves et al. |
| 2006/0207890 A1 | 9/2006 | Staud |
| 2007/0070549 A1 | 3/2007 | Suzuki et al. |
| 2007/0245909 A1 | 10/2007 | Homola |
| 2008/0075845 A1 | 3/2008 | Sonobe et al. |
| 2008/0093760 A1 | 4/2008 | Harper et al. |
| 2009/0117408 A1 | 5/2009 | Umezawa et al. |
| 2009/0136784 A1 | 5/2009 | Suzuki et al. |
| 2009/0169922 A1 | 7/2009 | Ishiyama |
| 2009/0191331 A1 | 7/2009 | Umezawa et al. |
| 2009/0202866 A1 | 8/2009 | Kim et al. |
| 2009/0311557 A1 | 12/2009 | Onoue et al. |
| 2010/0143752 A1 | 6/2010 | Ishibashi et al. |
| 2010/0190035 A1 | 7/2010 | Sonobe et al. |
| 2010/0196619 A1 | 8/2010 | Ishiyama |
| 2010/0196740 A1 | 8/2010 | Ayama et al. |
| 2010/0209601 A1 | 8/2010 | Shimokawa et al. |
| 2010/0215992 A1 | 8/2010 | Horikawa et al. |
| 2010/0232065 A1 | 9/2010 | Suzuki et al. |
| 2010/0247965 A1 | 9/2010 | Onoue |
| 2010/0261039 A1 | 10/2010 | Itoh et al. |
| 2010/0279151 A1 | 11/2010 | Sakamoto et al. |
| 2010/0300884 A1 | 12/2010 | Homola et al. |
| 2010/0304186 A1 | 12/2010 | Shimokawa |
| 2011/0097603 A1 | 4/2011 | Onoue |
| 2011/0097604 A1 | 4/2011 | Onoue |
| 2011/0171495 A1 | 7/2011 | Tachibana et al. |
| 2011/0206947 A1 | 8/2011 | Tachibana et al. |
| 2011/0212346 A1 | 9/2011 | Onoue et al. |
| 2011/0223446 A1 | 9/2011 | Onoue et al. |
| 2011/0241022 A1 | 10/2011 | Masuda |
| 2011/0244119 A1 | 10/2011 | Umezawa et al. |
| 2011/0299194 A1 | 12/2011 | Aniya et al. |
| 2011/0311841 A1 | 12/2011 | Saito et al. |
| 2012/0069466 A1 | 3/2012 | Okamoto et al. |
| 2012/0070692 A1 | 3/2012 | Sato et al. |
| 2012/0077060 A1 | 3/2012 | Ozawa |
| 2012/0127599 A1 | 5/2012 | Shimokawa et al. |
| 2012/0127601 A1 | 5/2012 | Suzuki et al. |
| 2012/0129009 A1 | 5/2012 | Sato et al. |
| 2012/0140359 A1 | 6/2012 | Tachibana |
| 2012/0141833 A1 | 6/2012 | Umezawa et al. |
| 2012/0141835 A1 | 6/2012 | Sakamoto |
| 2012/0148875 A1 | 6/2012 | Hamakubo et al. |
| 2012/0156523 A1 | 6/2012 | Seki et al. |
| 2012/0164488 A1 | 6/2012 | Shin et al. |
| 2012/0170152 A1 | 7/2012 | Sonobe et al. |
| 2012/0171369 A1 | 7/2012 | Koike et al. |
| 2012/0175243 A1 | 7/2012 | Fukuura et al. |
| 2012/0189872 A1 | 7/2012 | Umezawa et al. |
| 2012/0196049 A1 | 8/2012 | Azuma et al. |
| 2012/0207919 A1 | 8/2012 | Sakamoto et al. |
| 2012/0225217 A1 | 9/2012 | Itoh et al. |
| 2012/0251842 A1 | 10/2012 | Yuan et al. |
| 2012/0251846 A1 | 10/2012 | Desai et al. |
| 2012/0276417 A1 | 11/2012 | Shimokawa et al. |
| 2012/0308722 A1 | 12/2012 | Suzuki et al. |
| 2013/0040167 A1 | 2/2013 | Alagarsamy et al. |
| 2013/0071694 A1 | 3/2013 | Srinivasan et al. |
| 2013/0165029 A1 | 6/2013 | Sun et al. |
| 2013/0175252 A1 | 7/2013 | Bourez |
| 2013/0216865 A1 | 8/2013 | Yasumori et al. |
| 2013/0230647 A1 | 9/2013 | Onoue et al. |
| 2013/0314815 A1 | 11/2013 | Yuan et al. |
| 2014/0011054 A1 | 1/2014 | Suzuki |
| 2014/0044992 A1 | 2/2014 | Onoue |
| 2014/0050843 A1 | 2/2014 | Yi et al. |
| 2014/0151360 A1 | 6/2014 | Gregory et al. |
| 2014/0234666 A1 | 8/2014 | Knigge et al. |

DETERMINING STORAGE MEDIA SUBSTRATE MATERIAL TYPE

BACKGROUND

The present disclosure relates to the manufacturing of recordable media, and more specifically to quality control methods for the storage media substrates.

Manufacturing processes for recordable media may include substrate materials of various types, upon which layers of magnetic or other material are added through sputtering or other deposition processes. Moreover, at various times a manufacturing facility may produce recordable media using different substrate materials, perhaps even using common equipment to produce the media in separate batches or processes. Following the material deposition onto the substrates, however, the different substrate materials may be difficult or impossible to visually or optically distinguish.

BRIEF DESCRIPTION OF THE SEVERAL VIEWS OF THE DRAWINGS

So that the manner in which the above recited aspects can be understood in detail, a more particular description of embodiments of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation. The illustrations referred to here should not be understood as being drawn to scale unless specifically noted. Also, the drawings are often simplified and details or components omitted for clarity of presentation and explanation. The drawings and discussion serve to explain principles discussed below, where like designations denote like elements.

DETAILED DESCRIPTION

According to one embodiment, a method is provided for determining a material type of at least one storage media substrate. The method includes using a first sensor to detect an object that indicates the presence of the at least one storage media substrate. The method further includes using an inductive sensor to determine whether the at least one storage media substrate is of a metallic type.

According to another embodiment, a system is provided that includes a controller comprising a processor and that, when in operation, determines a material type of at least one storage media substrate. The system further includes a first sensor coupled to the controller for detecting an object that indicates the presence of the at least one storage media substrate, and an inductive sensor coupled to the controller for determining whether the at least one storage media substrate is of a metallic type.

According to another embodiment, a computer readable medium is provided. The computer readable medium contains a program which, when executed, performs an operation for determining a material type of at least one storage media substrate that includes using a first sensor to detect an object that indicates the presence of at the at least one storage media substrate. The operation further includes using an inductive sensor to determine whether the at least one storage media substrate is of a metallic type.

By detecting material types for storage media substrates after material deposition, inadvertent mistakes such as the mixing of substrate types may be avoided. Further, the techniques disclosed herein permit material types to be detected for multiple substrates included within a carrying cassette, which may help accelerate the completion and improve the accuracy of the manufacturing and distribution processes for the recordable media.

Figure 1:
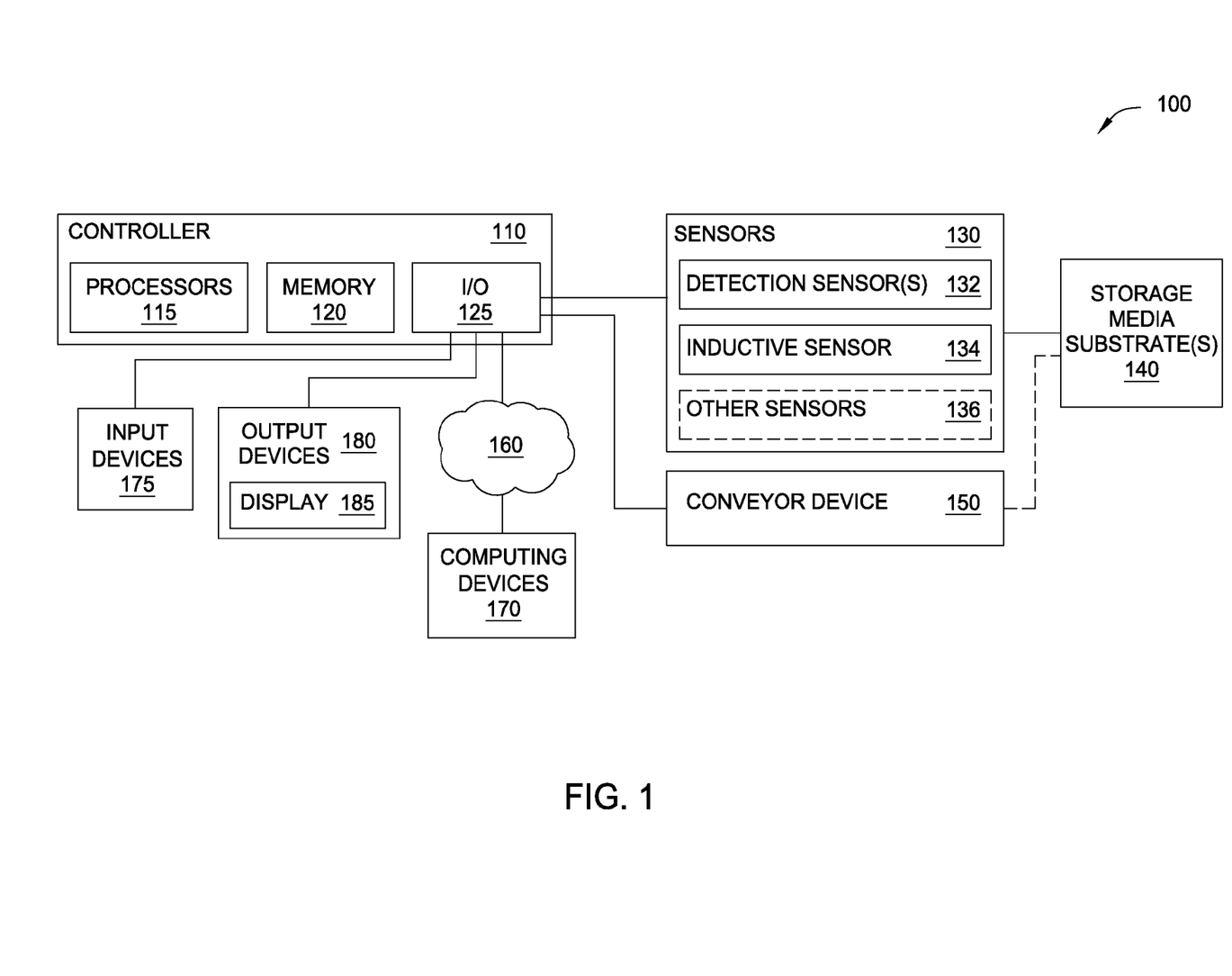
FIG. 1 illustrates an example environment for determining material types of storage media substrates, according to embodiments described herein.

FIG. 1 illustrates an example environment for determining material types of storage media substrates, according to embodiments described herein. In one embodiment, the environment may represent a discrete, standalone system for determining storage media substrate material type. In another embodiment, the environment may be a modular unit within a larger manufacturing environment for the storage media. In yet another embodiment, the functionality described below may be fully integrated into the manufacturing environment, so that the system need not appear as a distinct unit.

Environment 100 includes a controller 110 that is generally configured to perform the processing, interfacing, and coordinating for determining the storage media substrate material type. Controller 110 may include any suitable computing device, such as a general purpose computer that executes software for performing the various functions described herein. Controller 110 may also include any suitable computing module, such as firmware or an application-specific integrated circuit, that is included as part of a larger computing device or system. Controller 110 may also include industrial computing devices commonly used within manufacturing environments, such as a programmable logic controller (PLC).

Controller 110 includes one or more processors 115, which may include any processing element capable of performing the functions described herein. While depicted as a single element within controller 110, processors 115 are intended to represent a single processor, multiple processors, a processor or processors having multiple cores, as well as combinations thereof. The memory 120 may include a variety of computer readable media selected for their size, relative performance, or other capabilities: volatile and/or non-volatile media, removable and/or non-removable media, etc. Memory 120 may include cache, random access memory (RAM), storage, etc. Memory 120 may include one or more discrete memory modules, such as dynamic RAM (DRAM) dual inline memory modules (DIMMs). Of course, various memory chips, bandwidths, and form factors may alternately be selected. Storage included as part of memory 120 may typically provide a non-volatile memory for the controller 110, and may include one or more different storage elements such as Flash memory, a hard disk drive, a solid state drive, an optical storage device, and/or a magnetic storage device.

The controller 110 may communicate with other devices, such as peripheral devices or other networked computing devices, using one or more input/output (I/O) interfaces 125. I/O interfaces 125 may include a number of different I/O adapters providing various functionalities to the controller 110. For example, the controller 110 using I/O interfaces 125 may be configured to communicate with one or more users through input devices 175 (such as a keyboard, mouse, etc.), and one or more output devices 180, such as a display 185. The input devices 175 and output devices 180 may be provided as part of a human-machine interface (HMI) capable of controlling aspects of the manufacturing process of the storage media. Certain input devices 175 and output devices 180 may be provided as an integrated device (such as a touchscreen). I/O interfaces 125 may also include network interfaces that couple the controller 110 to networked computing devices 170 through a network 160. Network 160 may include one or more networks of various types, including a local area or local access network (LAN), a general wide area network (WAN), and/or a public network (e.g., the Internet).

I/O interfaces 125 may also permit the controller 110 to couple to one or more sensors 130 for sensing storage media substrates 140, and to a conveyor device 150 for providing relative motion between the sensors 130 and the storage media substrates 140. Sensors 130 include sensors of different varieties that are able to sense different qualities, characteristics, or properties of the storage media substrates 140, and to provide appropriate data to the controller 110. The storage media substrates 140 may be of any feasible shapes and sizes, and may comprise various types of materials. In one embodiment, the storage media substrates may be relatively thin, round disks (with center holes), which may be coated with magnetic material to create magnetic platters used for data storage in a hard disk drive. In one embodiment, the types of media substrates may be selected between relatively broad categories of materials, such as metallic and generally non-metallic; for example, a metallic substrate may be made of aluminum, while a non-metallic substrate may be made of glass. In other examples, the types of media substrates may include different materials within a single category, or different mixtures of materials such as metal alloys or composites. The different materials and/or mixtures may provide varying beneficial characteristics for the produced media, and the types of sensors 130 may be specifically selected so as to detect the differences between the types of substrates.

Including different types of sensors 130 may allow for cueing (where a measurement using one type of sensor may trigger a measurement using another type) and mixing (using the measurements of various sensors provides greater information about the sensed objects). The sensors 130 may be selected to complement each other; that is, one or more types of sensors are included to compensate for limitations of other types of included sensors. As shown, sensors 130 include a detection sensor 132 and an inductive sensor 134, and may optionally include other types of sensors 136. When detecting media substrates, the inductive sensor 134 may be able to compensate for limitations of the detection sensor 132, and vice versa. The sensors 130 may also be selected so that one type of sensor may be used to validate measurements taken by another type of sensor.

The detection sensor 132 may include a sensor of any feasible type that is capable of detecting the presence of an object, such as a storage media substrate or a cassette that may carry multiple substrates. Detection sensor 132 may detect objects using any known type of measurements, including chemical, mechanical, electrical, magnetic, optical, acoustic, thermal, and so forth. Detection sensor 132 is generally a transducer configured to convert the measurements into a signal suitable for processing by controller 110.

In one embodiment, detection sensor 132 comprises a photoelectric sensor that emits and receives a beam of light to provide data to the controller 110. The light may be of any suitable wavelength, such as visible light or infrared. The photoelectric sensor may generally detect the presence of objects by changes to the received light beam; for example, the properties of the detected object may cause modulation of the transmitted light beam, or the detected object may simply block some or all of the transmitted light beam from reaching the receiver. The photoelectric sensor may operate using any feasible sensing mode, such as opposed mode, retroreflective mode, or proximity mode. Depending on the desired sensing mode, the photoelectric sensor may include an emitter and receiver within a single housing, or may include separate emitter and receiver components. Photoelectric sensor may be disposed in any feasible configuration for sensing the storage media substrates 140. For example, the photoelectric sensors may generally be disposed at any position (e.g., a selected angle and distance) relative to a sensed portion of the storage media substrates 140. For embodiments using separate emitters and receivers, the emitter may be disposed on one side of the storage media substrate while the receiver is disposed on the other side of the storage media substrate. The portion of the storage media substrate that will be sensed by the photoelectric sensor may be selected as part of the greater storage media manufacturing process. The selection of a sensed portion may offer advantages that facilitate the manufacturing process, such as improved speed and accuracy of the sensing, or providing the storage media substrates in a housing or in a particular configuration helpful for subsequent manufacturing steps. In one example, a surface of the storage media substrate may be sensed. In another example, a side profile (i.e., a thickness) of the storage media substrate may be sensed. Housing multiple storage media substrates in a carrier or cassette will be discussed in more detail below.

Following the deposition of material on the storage media substrates, which may include the coating of one or more surfaces of the substrates, the different types of substrates may be difficult or impossible to visually distinguish. In turn, this may cause the utility of the photoelectric sensor to be reduced. While the photoelectric sensor may still be able to detect the presence of storage media substrates 140, it may no longer be able to distinguish the different types of the substrates. Inductive sensor 134 is configured to detect the proximity of metallic objects, generally by determining changes to the magnetic field that is established by a signal driven onto the inductive sensor 134. The inductive sensor may thus distinguish between metallic and substantially non-metallic types of storage media substrates, as well as between types of substrates having different amounts of a metal or having different metals, even though the differences between types of substrates may be visually indistinguishable. As defined herein, "substantially non-metallic" generally refers to materials having zero or a relatively low percentage of metal content, such that the materials when sensed would not produce a detectable change to the magnetic field established by the inductive sensor 134. Alternatively, any changes to the magnetic field by a substantially non-metallic material may fall within a noise tolerance for the inductive sensor 134, or may fall below some threshold amount based on a tuning of the inductive sensor.

In one embodiment, other sensors 136 may be included to provide additional information to distinguish the at least two types of media substrates, or to distinguish additional types of media substrates that may not be distinguishable using the sensors described above (i.e., detection sensor 132, inductive sensor 134). The other sensors 136 may operate in different ranges or along entirely different dimensions than the sensors described above. For example, other sensors 136 may include other passive or active sensors, such as capacitive sensors, infrared sensors, magnetic sensors, sonar sensors, radar sensors, lidar sensors, and so forth. Other sensors 136 may also include an imaging device, such as a charge-coupled device (CCD), that may be used to determine positional information for the storage media substrates.

In an alternate embodiment, the detection sensor 132 and the inductive sensor 134 may be replaced by another combination of at least two types of sensors. The combination may be selected to distinguish between different types of storage media substrates, such as those particular types which are produced in a particular manufacturing facility.

Conveyor device 150 may be included for providing relative motion between the sensors 130 and the storage media substrates 140. The conveyor device 150 may include any suitable mechanized or motorized means for moving objects, and the motion may be controlled by the controller 110. The conveyor device 150 may also provide lateral and/or subjacent support for the moving objects. Some examples of conveyor device 150 include a motorized conveyor belt or track, electric rail assembly, chain drive, pulley system, robotic arm, and so forth. The conveyor device 150 may be a distinct device from the sensors 130 and storage media substrates 140, or may be integrated with one or both of these and/or with a substrate carrier. In an alternative embodiment, the conveyor device 150 is optional, and relative motion between the sensors 130 and storage media substrates 140 may (also) be provided manually.

The conveyor device 150 may generally increase the automation, speed, and efficiency of determining material types for a plurality of media substrates 140. As will be discussed below, conveyor device 150 may be used for rapidly sensing media substrates carried in cassettes or other carriers. In one embodiment, the conveyor device 150 moves the media substrates 140 (and a cassette, if included) relative to fixed sensors 130. In another embodiment, the conveyor device 150 moves the sensors 130 relative to the storage media substrates 140, which may be fixed. In another embodiment, both the sensors 130 and storage media substrates 140 are movable.

Figure 2A:
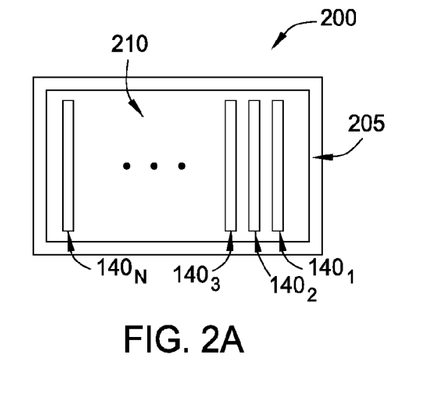
FIGS. 2A and 2B illustrate example cassettes for storage media substrates, according to embodiments described herein.
Figure 2B:
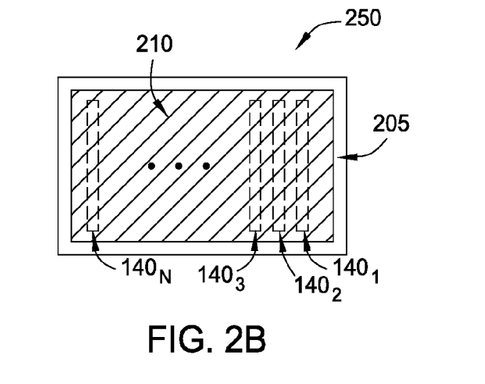

FIGS. 2A and 2B illustrate example cassettes for storage media substrates, according to embodiments described herein. Open cassette 200 and closed cassette 250 (collectively referred to as "cassettes") may generally be used in environment 100 and may carry a plurality of storage media substrates, each of which may include deposition layers that are added during manufacturing processes. Each of the plurality of storage media substrates may have a respective material type that may be determined using a plurality of sensors (such as sensors 130).

FIGS. 2A and 2B provide a top view of the cassettes 200, 250. In addition to their utility for determining material types of the storage media substrates, the cassettes 200, 250 may generally be provided for convenient transport of multiple storage media substrates during manufacturing processes. The cassettes 200, 250 may be constructed of any feasible material for carrying the storage media substrates 140. In some embodiments, the cassettes 200, 250 may be visually detectable by sensors (such as a photoelectric sensor), but are not detectable along the same dimension(s) as those used to distinguish different types of media substrates. In other words, if the controller were configured to distinguish between types of media substrates using an inductive sensor, the cassette 200, 250 should not be made of a metal or alloy, as the presence of the cassette may cause errors or other detrimental effects to sensing the storage media substrates using the inductive sensor. In one embodiment, components of the cassette 200, 250 may be constructed using a transparent, translucent, or opaque plastic material, which may partially or completely obstruct the visibility of any storage media substrates 140 within the cassette.

Though a top view is depicted here, in alternate embodiments the cassettes 200, 250 may be oriented in any manner consistent with the positions of the sensors used to detect the storage media substrates 140, so that FIGS. 2A and 2B could alternately represent a side view, bottom view, etc. of the cassettes 200, 250.

Cassettes 200, 250 includes one or more walls 205 enclosing a volume 210, in which one or more storage media substrates $140_1$-$140_n$ are disposed. Open cassette 200 differs from closed cassette 250 in that cassette 200 includes at least one opening in the walls 205 so that the storage media substrates 140 may be visible through the opening(s) to certain types of sensors, such as a photoelectric sensor. In one embodiment, the opening in cassette 200 may be filled using a removable top wall 260 to produce the closed cassette 250. When the top wall 260 is emplaced, as in FIG. 2B, the visibility of the storage media substrates 140 may be obscured or obstructed (denoted by dashed lines), so that a photoelectric sensor may not be able to clearly distinguish the media substrates when viewed through the top wall 260. In an alternate embodiment, closed cassette 250 may not include any removable walls, but may be formed as a unitary construction, or may include multiple walls that are secured together during the process of scanning storage media substrates 140.

In another embodiment, open cassettes 200 may include a plurality of openings, which may be positioned relative to walls 205 to allow multiple sensors to sense the storage media substrates from different positions and/or relative angles. In one embodiment, an opposed mode photoelectric sensor may include an emitter located near a first opening of the cassette 200, and a receiver located near a second opening of the cassette 200. Because the emitter and receiver are aligned during operation, the opposed mode photoelectric sensor may sense at least a portion of storage media substrates that are located between the first and second openings. For example, open cassette 200 may have removable top and bottom walls that generally oppose each other.

The storage media substrates 140 may be arranged in any suitable configuration within the volume 210. As shown, the storage media substrates 140 are disposed transverse to the length of cassettes 200, 250 and are substantially parallel to each other. The storage media substrates 140 may further be coaxially aligned within the cassette; as shown, the axis of alignment is substantially parallel to the length of cassette 200, and may be centered within the cassette. The storage media substrates 140 may be held in relatively fixed positions within the cassettes 200, 250 using various known means that provide support and/or spacing for the substrates, such as slots disposed on the one or more walls 205, a separate framing device (such as a rack) within the volume 210, a spindle inserted through center holes of storage media substrates 140 with spacers included between adjacent substrates, and so forth.

Figure 3A:
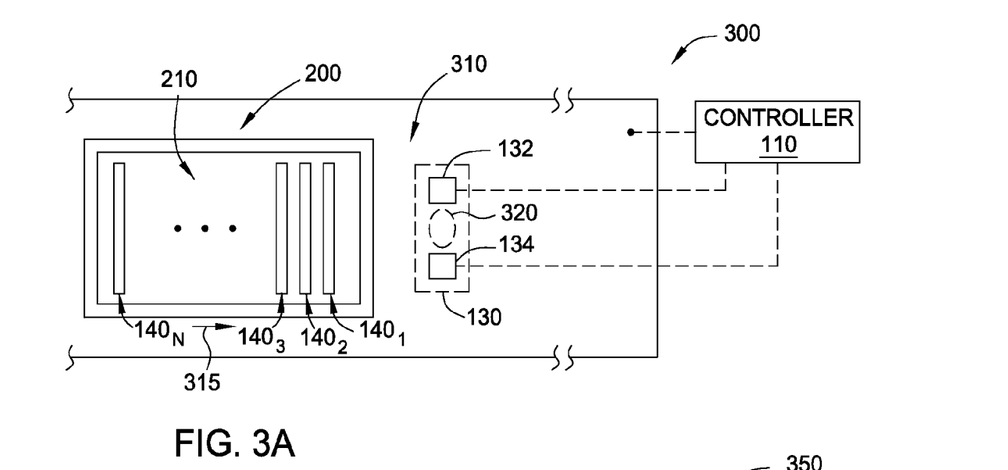
FIGS. 3A-3C illustrate example sensing systems for determining material types of storage media substrates, according to embodiments described herein.
Figure 3B:
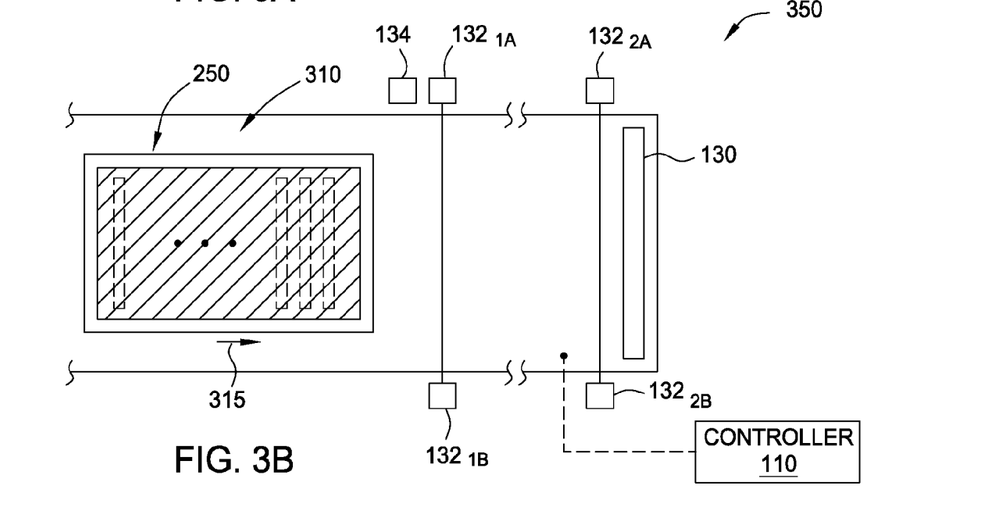

FIGS. 3A and 3B illustrate example systems for determining material types of storage media substrates, according to embodiments described herein. The sensing systems 300, 350 may generally be used within environment 100, and may include cassettes for carrying a plurality of storage media substrates, such as cassettes 200, 250 described above.

As shown, sensing system 300 includes an open cassette 200 that may be moved relative to sensors 130 using a conveyor belt 310. Open cassette 200 includes a plurality of storage media substrates 140, which may include substrates of different material types. Of course, any other type of conveyor device may provide the relative motion between the storage media substrates 140 and the sensors 130, consistent with the description of conveyor devices above.

Sensors 130 include a detection sensor 132 and inductive sensor 134. As shown, the sensors are disposed above the conveyor belt 310 and above the open cassette 200, and are oriented to sense downward (i.e., toward the conveyor belt). The sensors 130 may be physically coupled (included in a common housing, coupled to a common platform, etc.) or separately arranged. Each of the sensors is also disposed within a respective maximum sensing range from the storage media substrates 140 located within the open cassette 200, so that the sensors are able to effectively detect the substrates. The sensors 130 may be configured to sense a side profile of the storage media substrates 140, and/or may be configured to sense a portion of one or more surfaces of the substrates. Of course, the sensors 130 may be disposed in different arrangements than those examples depicted in FIGS. 3A and 3B. The sensors may be disposed at various positions and orientations relative to the storage media substrates 140, such as laterally outward from the substrates and/or cassettes 200, 250 with each sensor on an opposing side. Each of the sensors 130 may be aligned relative to each other in order to sense in a common sensing region 320. The common sensing region 320 may also correspond to a common sensed portion of storage media substrates 140. The common sensed portion of the storage media substrates 140 may correspond to portions disposed near the top of the cassette or at any other regions of the storage media substrates (such as near a center point) The size and/or location of the common sensing region 320 may be selected to provide a suitable resolution for detecting the storage media substrates 140 and for determining a material type for each. For example, if the width of the common sensing region 320 is too large, multiple substrates could be captured within a single sensor measurement, and so the sensors may be unable to distinguish each substrate in order to determine its material type. Of course, in other embodiments, the sensors 130 may have distinct sensing regions that are not shared with other sensors, and correspond to different sensed portions of the storage media substrates 140.

Controller 110 is configured to control the movement of conveyor belt 310, as well as the sensing measurements of the sensors 130. While FIG. 3A depicts one possible configuration (i.e., a particular combination of sensors in a particular arrangement), other configurations are possible. In one embodiment, the sensors may have different positions and orientations. For example, the detection sensor 132 may be disposed above the cassette 200 to sense the storage media substrates 140 through an opening 210. However, the inductive sensor 134 does not need to be oriented to sense through the opening, but can sense the media substrates from nearly any orientation relative to the cassette 200. Of course, the inductive sensor 134 would need to remain within its maximum sensing range from the storage media substrates, and may also require the walls of the cassette 200 (and any other objects within the sensing path) to be substantially non-metallic so as not to interfere with measurements of the inductive sensor.

In one embodiment, detection sensor 132 and inductive sensor 134 sense at overlapping times, or at substantially the same time. The sensing performed may be performed continuously, or may be sampled at discrete time periods. The controller 110 may synchronize the timing of the sampling to match the positions of the cassette and/or substrates as each passes through the sensing region 320. The positions may be known to the controller 110 or may be easily estimated, as the movement of the conveyor device (such as conveyor belt 310) is also controlled by the controller. Controller 110 may include a counter in memory to track the number of substrates detected for a particular cassette, which may correspond to cassettes that hold a known number of substrates. Alternatively, the controller 110 may sense using another sensor (i.e., corresponding to other sensors 136) to determine overall substrate positions within a cassette. For example, the controller 110 may use a camera to take a snapshot of the cassette, and may perform image processing on the snapshot to determine a number of substrates for the cassette and/or the particular substrate that is concurrently sensed by the sensors 130.

In another embodiment, detection sensor 132 and inductive sensor 134 performed sequenced sensing (also "cueing"). That is, one of the sensors performs sensing, whether continuously or discretely, while the other of the sensors is not sensing. Upon detecting a particular measurement from the sensing sensor, the controller also senses using the other sensor. Discrete sampling and sequenced sampling may generally provide energy savings for the sensing system 300, as controller 110 would not need to drive or detect both sensors continuously.

In one embodiment, the inductive sensor 134 performs sensing while detection sensor 132 is not sensing. When the inductive sensor 134 indicates that a metallic object (such as a substrate) is detected, the controller may responsively drive detection sensor 132 to validate the inductive sensor's signal. If the expected object is also detected by the detection sensor 132, operation may proceed. However, if detection sensor 132 fails to detect the expected object, this may indicate a malfunction of at least one of the sensors, and the controller 110 may generate an alarm or otherwise record the error. Of course, the sensing sequence may alternatively be performed in the reverse order (i.e., detection sensor 132 operates and inductive sensor 134 is responsively driven based on a value provided by detection sensor 132).

Sequenced sensing may be used with other sensors, such as the camera discussed above. For example, the camera may take a snapshot of the cassette or of certain substrates in response to the detection sensor 132 detecting the presence of the cassette or a first substrate.

Sequenced sensing may also be used in the case of a closed cassette, in which the detection sensor 132 may be able to detect the cassette but unable to detect the substrates carried by the cassette. Closed cassettes will be discussed further with respect to FIG. 3B. For example, the controller 110 may operate the detection sensor, and upon detecting an object (i.e., the closed cassette) controller 110 may activate the inductive sensor 134 to detect the substrates carried by the cassette. The controller 110 may add a small delay before sensing with the inductive sensor 134, to compensate for the expected distance between the sensed wall of the closed cassette and the first substrate within the cassette. Alternatively, the detection sensor 132 may detect the cassette at approximately the same time that the inductive sensor 134 detects the first substrate in the cassette. For example, a common sensing region 320 may be wide enough to include both the sensed wall and the expected position of the first substrate at the same time, or the sensors 130 may be aligned differently to compensate for the expected distance (such that there may be a smaller common sensing region 320, or no common sensing region at all).

Alarms may be generated by the controller 110 to indicate malfunctions of components of the sensing system 300, as well as indicating various conditions based on sensor measurements. The alarm conditions may be programmed by a user of the sensing system, and may be related to quality control for the storage media substrate manufacturing process. For example, the process may require that all slots within a cassette are filled with substrates, and that all of these substrates are of a single material type. Therefore, alarm conditions may exist when the sensors detect that at least one cassette slot is empty, and when the sensors detect that there is a mixture of different types of substrates within a cassette. The alarms may report the type of error (e.g., substrate missing, mixed substrates), as well as the cassette position of the substrate(s) in question (e.g., slots x and y). As discussed above, the controller 110 may have this positional information based on controlling the movement of the conveyor device, by counting a number of substrates detected, and/or by employing additional sensors such as a camera.

FIG. 3B depicts sensing system 350, which includes a closed cassette 250 that may be moved relative to sensors 130 using a conveyor belt 310. Sensing system 350 operates similarly to the sensing system 300, with additional considerations for the detection sensor 132 that may be unable to detect individual substrates due to the closed cassette 250. As discussed above, closed cassette 250 may have a unitary construction or may include one or more removable or separable walls, and may obscure or obstruct the ability of the detection sensor 132 (such as a photoelectric sensor) to detect the individual substrates.

The detection sensor and inductive sensor 134 may generally be disposed at any desired positions. As shown, the inductive sensor 134 is disposed to sense through a side wall of the closed cassette 250. The detection sensor is an opposed mode photoelectric sensor with a separate emitter element $132_{1A}$ and receiver element $132_{1B}$. The detection sensor may be disposed alongside the inductive sensor and configured to sense in the same direction (as shown) or may be disposed in any suitable alternate position (say, above the cassette, along a different side as the inductive sensor 134, or at a different elevation along the same side of the cassette). The distance between the detection sensor and inductive sensor 134 may be approximately the same as the expected distance between the leading edge of the cassette and the position of the first substrate in the cassette, or the sensors may be relatively aligned to detect the leading edge and the first substrate nearly simultaneously.

Sensing system 350 may also include a second detection sensor disposed along conveyor belt 310 that may indicate to the controller 110 that based on the position of the closed cassette 250, the controller may stop sensing on at least one of the first detection sensor and inductive sensor 134. The sensing system 350 may also include a physical stop 360 that halts the movement of the closed cassette along the conveyor belt 310. As shown, second detection sensor includes a second opposed mode photoelectric sensor $132_{2A}$, $132_{2B}$ is disposed along the conveyor belt 310, further along the direction of motion indicated by arrow 315. The distance between the first detection sensor $132_{1A}$, $132_{1B}$ and the second detection sensor $132_{2A}$, $132_{2B}$ may be selected as the approximate length of closed cassette 250. Alternatively, the distance may be selected as the approximate distance between the leading edge of the closed cassette 250 and the expected position of the last substrate slot within the closed cassette. In either case, when the second detection sensor $132_{2A}$, $132_{2B}$ detects the presence of the cassette, controller 110 may stop sensing using the inductive sensor 134 and/or the first detection sensor $132_{1A}$, $132_{1B}$, as no additional storage media substrates from the closed cassette 250 are expected to pass through the respective sensing regions.

Detecting the material type of the storage media substrates carried by the closed cassette 250 may be performed in several different ways. In one example, the controller 110 may control the movement of the conveyor so that discrete sensor samples are taken using inductive sensor 134 at times that correspond to expected positions of the substrates within the closed cassette 250. Of course, the detection sensor may not be able to detect the presence of an individual substrate within the closed cassette 250, so controller 110 may rely on the combination of the presence of the cassette (detected by the detection sensor) and the discrete measurements of the inductive sensor 134 to determine whether or not a metallic substrate is present at an expected position. When the inductive sensor 134 determines that a metallic substrate is not present at one or more positions of the closed cassette, this may indicate that (i) no substrate is present at the position, (ii) a non-metallic substrate is present at the position, and/or (iii) the controller's timing is not properly synchronized, so that the inductive sensor 134 is not sensing at a time when a substrate is passing through the corresponding sensing region. In any of these cases, an alarm may be generated by the controller 110 indicating that further inspection may be required by a user of the sensing system 350 (for example, an operator working along the manufacturing line for the substrates). The controller 110 may also be able to indicate which substrate position (e.g., slot x) triggered the error, using an index of the discrete sensing measurement or a different counter.

In another example, the controller 110 may continuously sense material types of the substrates using the inductive sensor 134. The period of continuous sensing may be triggered when the (first) detection sensor detects the presence of the closed cassette 250, and may end when the first detection sensor no longer detects the cassette or when the second detection sensor detects the cassette. During the period of continuous sensing, inductive sensor 134 senses a continuous signal, which may be provided to the controller 110 as an analog signal. Alternatively, the inductive sensor may include a threshold tuning or other logic that determines a logical output (corresponding to "metallic substrate detected" or "no metallic substrate detected" states) that is provided to the controller 110. The continuous sensed signal may have fluctuations that are caused by the movement of the substrates through the sensing region, which in some cases may reflect the combined effect of two or more substrates on the inductive sensor 134. Depending on the size of the sensing region, the continuous signal to the controller 110 may also include local minima, which may generally correspond to a maximum distance from the sensing region to any one substrate. For example, the continuous signal could experience a local minimum at the midpoint between two consecutive metallic substrates.

For a defined error condition, such as a missing substrate or a non-metallic substrate mixed with the metallic substrates, the values of the continuous signal may be substantially less than the values of local minima. Correspondingly, a threshold value may be set relative to the expected values of local minima (either at the inductive sensor 134 or the controller 110) so that values of the continuous signal less than the threshold cause the controller 110 to generate an alarm.

In another example, the controller 110 may be further configured to determine that a cassette includes only non-metallic storage media substrates, such as glass substrates. Admittedly, a controller 110 merely using inductive sensor 134 to detect material types of the substrates may not be capable of distinguishing the presence of a non-metallic substrate from the absence of a substrate, but other types of sensors may be included to either directly sense the substrate, or to indirectly gather information that may suggest presence or absence of the substrate (such as a checkweigher measuring the total weight of the cassette including the substrates). In any case, controller 110 is able to determine that a metallic storage media substrate is included in a cassette that is otherwise expected to contain non-metallic substrates, and may generate an alarm to indicate that further inspection is required for the cassette.

Figure 3C:
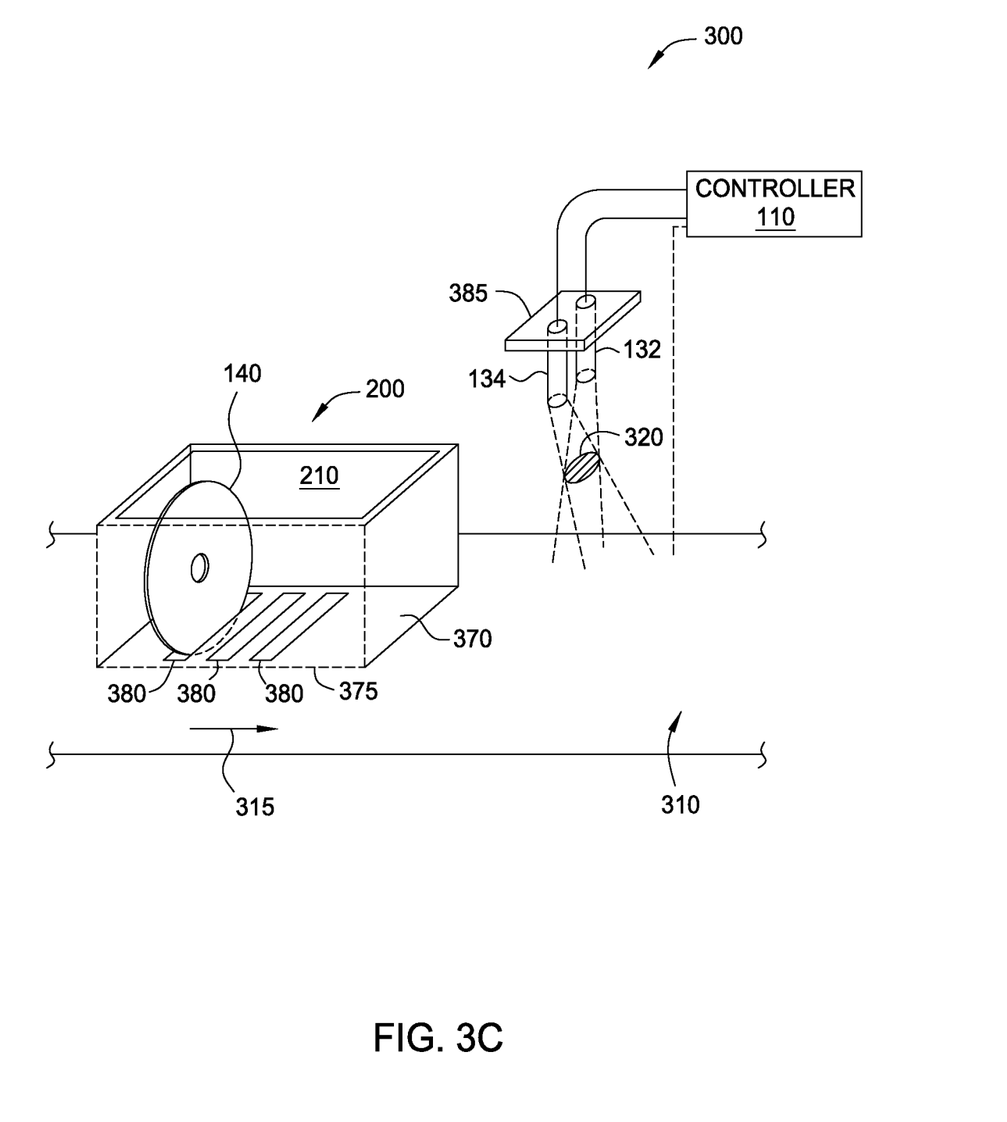

FIG. 3C depicts an alternate projection of the sensing system 300, according to one embodiment. While open cassette 200 is included for clarity of the depiction, the principles and techniques may also be applied to closed cassettes and in alternate sensing systems and environments. Open cassette 200 includes one or more walls 370, including a cutaway of wall 375 (indicated by a dashed line) which is included for clarity of the depiction. The open cassette 200 includes a plurality of discrete slots 380 included in a bottom wall of the cassette, with each slot 380 configured to hold a respective storage media substrate 140. Of course, slots may be included in different walls, or alternate support and spacing devices provided, consistent with the descriptions provided above.

As shown, detection sensor 132 and inductive sensor 134 are disposed above conveyor belt 310 and are mounted to a common structure 385. The open cassette 200 and storage media substrates 140 are configured to move along conveyor belt 310 in the direction of arrow 315. The sensors 132, 134 are arranged to sense in a direction substantially perpendicular to the movement of the cassette and substrates, and generally detect a side profile of the substrates. The sensors 132, 134 share a common sensing region 320, which is selected to correspond to a portion of the storage media substrates 140 as each passes through the sensing fields. As shown, the common sensing region 320 roughly corresponds to a top portion of the storage media substrates 140.

Figure 4:
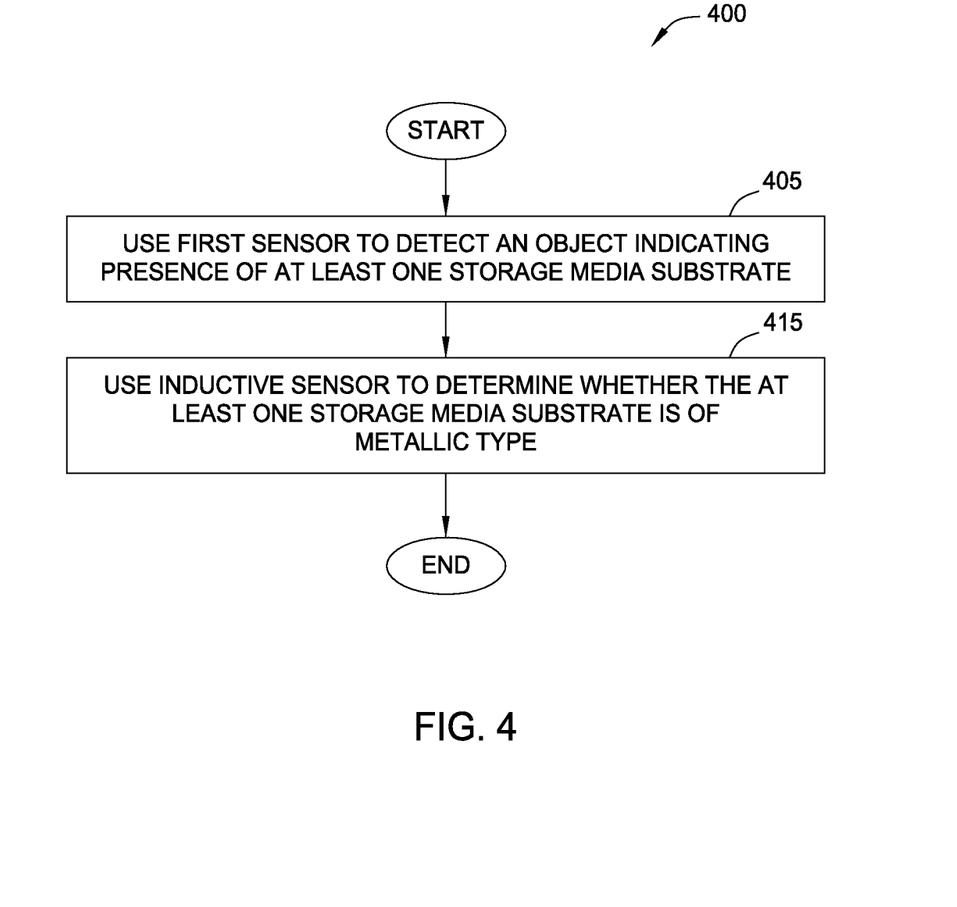
FIG. 4 illustrates a method for determining material types of storage media substrates, according to embodiments described herein.

FIG. 4 illustrates a method for determining material types of storage media substrates, according to embodiments described herein. Method 400 may generally be used with the sensing systems, cassettes, and storage media substrates described in various embodiments above.

Method 400 begins at block 405, where a first sensor is used to detect an object that indicates the presence of at least one storage media substrate. The object may be a storage media substrate, or a cassette capable of carrying a plurality of storage media substrates. The first sensor may detect the presence or absence of objects using any known type of measurements, including chemical, mechanical, electrical, magnetic, optical, acoustic, thermal, and so forth. The cassette and/or storage media substrates may be moved into a sensing region for the first sensor using a conveyor device.

At block 415, an inductive sensor is used to determine whether the at least one storage media substrate is of a metallic type. A controller that receives data from the inductive sensor and from the first sensor may generate an alarm when the inductive sensor does not detect a metallic substrate (when a metallic substrate is expected), and may report the type of error (e.g., a substrate missing or mixed substrates within the cassette), as well as the cassette position of the substrate(s) in question. Likewise, the controller may generate an alarm when the inductive sensor detects a metallic substrate (when a non-metallic substrate is expected). The method ends following completion of block 415.

Blocks 405 and 415 may be performed in any sequence, and may be performed at the same time, at partially overlapping times, or at different times. The sensing performed in these blocks may be continuous or discrete, or combinations thereof.

Figure 5:
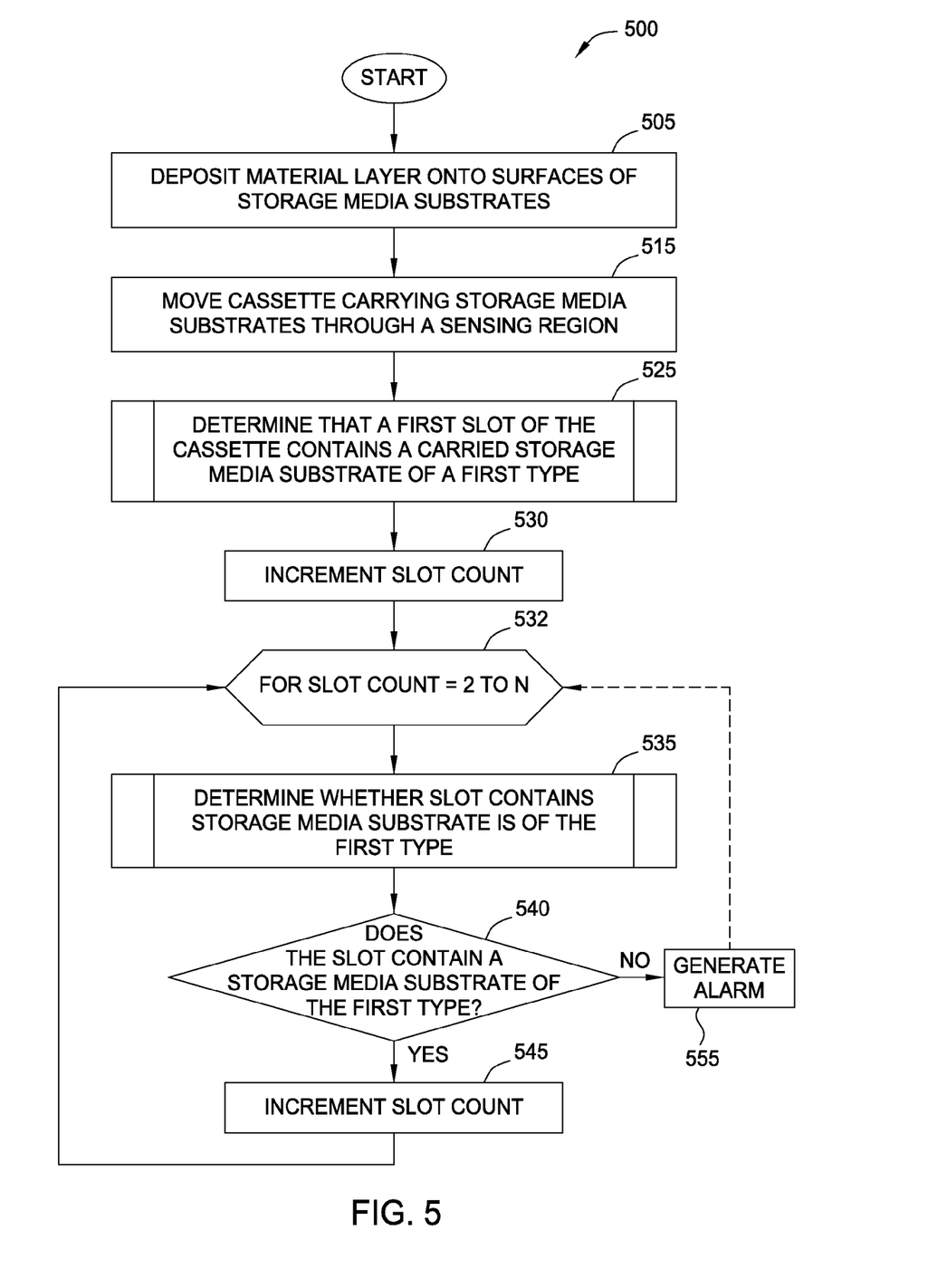
FIG. 5 illustrates a method for manufacturing storage media substrates, according to embodiments described herein.

FIG. 5 illustrates a method for manufacturing storage media substrates, according to embodiments described herein. Method 500 may generally be used in conjunction with the sensing systems, cassettes, and storage media substrates described in various embodiments above.

Method 500 begins at block 505, where a material layer is deposited onto one or more surfaces of a plurality of storage media substrates. The material layer (or layers) may include a magnetic material or any other type of material suitable for use as a memory, and may be deposited according to any known methods. The surfaces may include different surfaces of the storage media substrate, such as opposing surfaces of the substrate. In some embodiments, the material type of the storage media substrate may be obscured from detection by certain sensors by the deposited layers. For example, deposited layers may prevent an optical sensor from detecting the material type of the storage media substrate. At block 515, a cassette carrying the storage media substrates is moved through a sensing region. The relative motion between the cassette (and carried storage media substrates) and the sensors may be provided by any known devices for moving objects, such as mechanized or motorized devices. The sensing region may include a common sensing region shared by a plurality of sensors, or may include separate regions for different sensors.

At block 525, the type of a first carried storage media substrate is determined. The first carried storage media substrate may correspond to a particular slot or predetermined position within the cassette. Determining the type of the storage media substrate may generally be performed in accordance with method 400, described above. In an alternative embodiment, the type of the first storage media substrate may be determined without reference to a known (or estimated) slot or position within the cassette.

At block 530, after the first slot has been determined to contain a storage media substrate of a first type, a count of the cassette slots is incremented. The count may be maintained by a controller so that collected sensor data may be associated with individual various storage media substrates during the process. The count may also be used to verify that the expected number of slots or storage media substrates within the cassette has been detected. Differences in the count may indicate misalignment of the sensors, cassette, or storage media substrates, missing storage media substrates within the cassette, a mixture of storage media substrate types within the cassette, or various other alarm conditions. In an alternative embodiment, the count may be incremented to reflect a number of storage media substrates of one (or of each) determined type.

At block 535, and for a slot count of 2 to a predetermined number N, the types of the carried storage media substrates are determined. Again, this determining may be performed according to method 400, described above. In one embodiment, N may represent the number of storage media substrates actually contained within the cassette (i.e., an actual count irrespective of material type), so that the for-loop continues until the last storage media substrate is detected. In another embodiment, N may represent the number of storage media substrates of the first type (i.e., an actual count of the storage media substrates that match the type of the first storage media substrate). In another embodiment, N may represent the expected number of storage media substrates or slots within the cassette (i.e., an expected count). Each iteration of the for-loop generally corresponds to the cassette's movement through the sensing region, and the for-loop may end upon reaching the predetermined number N, or when the cassette is no longer detected.

In an alternative embodiment, and similar to the description for block 525, the type of subsequent storage media substrates may be determined without reference to a known (or estimated) slot or position within the cassette. In such an embodiment, maintaining a count may be optional, and the controller may be configured to continue detecting whether subsequent storage media substrates are of the first determined type. Even without reference to certain slots or positions within the cassette, the controller may operate to determine whether the cassette contains a mixture of two types of storage media substrates.

At block 540, when a particular slot is determined to contain a storage media substrate that is of the first type (i.e., matching the type of the storage media substrate contained in the first slot), the method proceeds to block 545, where the slot count is incremented before returning for the next iteration of the for loop. However, when the contents of a particular slot are determined to not include a storage media substrate of the first type, the method proceeds to block 555, where an alarm is generated. Determining that a particular cassette slot does not contain a storage media substrate of the first type may include an affirmative determination that the storage media substrate is of a second type, that no storage media substrate is present in the slot, that the sensor or cassette are misaligned, and so forth. Each of these possibilities may require further investigation and/or resolution before resuming the manufacturing process.

In some sensor and cassette configurations, it may not be possible to make an affirmative determination of the slot contents, but sensor data may be used to determine that whatever may be present or absent in a particular cassette slot, the slot does not contain a storage media substrate of the first type. For example, an optical sensor may not be able to determine whether a storage media substrate is located at any particular slot in a closed cassette due to opacity of the cassette, etc. However, an inductive sensor working in combination with the optical sensor may detect whether or not the slot includes a metallic storage media substrate, which may be matched against the first type.

In different embodiments, the method 500 may proceed differently after an alarm is generated in block 555. In one embodiment, the method 500 may end. In this case, the type(s) of remaining storage media substrates in the cassette may not be determined, but the alarm condition must be investigated and/or resolved before proceeding. In another embodiment, the method 500 returns to block 522 after generating the alarm without incrementing the slot count. In this case, the slot count may represent a count of the number of storage media substrates that are determined to match the first type. In another embodiment, the method 500 may proceed to block 545 and increment the slot count before returning to block 522. In this case, the slot count may represent a count of storage media substrates (of all material types).

The method 500 ends at the earliest of completing N−1 iterations of determining the cassette slot contents, when the sensors no longer detect the cassette, and (optionally) if a generated alarm condition causes the method to terminate.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Embodiments of the present disclosure may include a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present disclosure, other and further embodiments of the disclosure may be devised without departing from the basic scope thereof, and the scope thereof is determined by the claims that follow.

What is claimed is:

1. A method for determining a material type of at least one storage media substrate, the method comprising:
    using a first sensor, detecting an object that indicates the presence of the at least one storage media substrate; and
    using an inductive sensor, determining whether the at least one storage media substrate is of a metallic type.

2. The method of claim 1, wherein the detected object is a storage media substrate.

3. The method of claim 1, further comprising validating a signal from the inductive sensor by detecting the storage media substrate using the first sensor after determining the storage media substrate is of a metallic type.

4. The method of claim 1, wherein the detected object is a cassette carrying one or more storage media substrates, and wherein the first sensor is a photoelectric sensor, the method further comprising using a conveyor device to move the cassette into a light beam of the photoelectric sensor.

5. The method of claim 1, wherein the detected object is a cassette carrying one or more storage media substrates, the method further comprising:
    determining that a first slot of the cassette contains a first carried storage media substrate that is of a first type of a metallic type and a substantially non-metallic type; and
    generating an alarm upon determining that a second slot of the cassette does not contain a second carried storage media substrate of the first type.

6. The method of claim 5, wherein the cassette carries at least one substantially non-metallic storage media substrate that includes a glass substrate, and wherein the cassette carries at least one metallic type storage media substrate that includes an aluminum substrate.

7. The method of claim 1, wherein the material type is determined within a manufacturing process for a plurality of storage media substrates that includes the at least one storage media substrate, the method further comprising:
    depositing a material layer onto one or more surfaces of each of the plurality of storage media substrates, wherein the first sensor is unable to determine the material type of the plurality of storage media substrates;
    after depositing the material layer, and using a conveyor device, moving a cassette carrying the plurality of storage media substrates through a sensing region for the first sensor and for the inductive sensor, wherein the plurality of storage media substrates have a same orientation within the cassette, wherein the cassette is moved substantially perpendicular to the sensing region, and wherein the sensing region is selected to detect at least a side profile of each of the plurality of storage media substrates;
    determining that a first slot of the cassette contains a first carried storage media substrate that is of a first type of a metallic type and a substantially non-metallic type; and
    generating an alarm upon determining that a second slot of the cassette does not contain a second carried storage media substrate of the first type.

8. The method of claim 7, wherein determining that a second slot of the cassette does not contain a second carried storage media substrate of the first type includes one of detecting a carried storage media substrate of a second type and determining an absence of a carried storage media substrate from the second slot.

9. A system, comprising:
a controller comprising a processor and that, when in operation, determines a material type of at least one storage media substrate;
a first sensor coupled to the controller for detecting an object that indicates the presence of the at least one storage media substrate; and
an inductive sensor coupled to the controller for determining whether the at least one storage media substrate is of a metallic type.

10. The system of claim 9, wherein the first sensor operates to detect a storage media substrate.

11. The system of claim 9, wherein the controller, when in operation, validates a signal from the inductive sensor by detecting the storage media substrate using the first sensor after determining the storage media substrate is of a metallic type.

12. The system of claim 9, wherein the first sensor is a photoelectric sensor and operates to detect a cassette carrying one or more media substrates, and further comprising a conveyor device that operates to move the cassette into a light beam of the photoelectric sensor.

13. The system of claim 9, further comprising a cassette carrying one or more storage media substrates, and wherein the controller, when in operation:
determines that a first slot of the cassette contains a first carried storage media substrate of a first type of a metallic type and a substantially non-metallic type; and
generating an alarm upon determining that a second slot of the cassette does not contain a second carried storage media substrates of the first type.

14. The system of claim 13, wherein the cassette carries at least one substantially non-metallic storage media substrate that includes a glass substrate, and wherein the cassette carries at least one metallic type storage media substrate that includes an aluminum substrate.

15. The system of claim 9, further comprising a conveyor device that operates to move a cassette carrying a plurality of storage media substrates that includes the at least one storage media substrate through a sensing region for the first sensor and for the inductive sensor,
wherein the material type is determined within a manufacturing process for the plurality of storage media substrates,
wherein a material layer is deposited onto one or more surfaces of each of the plurality of storage media substrates before determining the material type of the plurality of storage media substrates,
wherein the first sensor is unable to determine the material type of the plurality of storage media substrates,
wherein the cassette is moved through and substantially perpendicular to the sensing region after depositing the material layer, and using the conveyor device,
wherein the plurality of storage media substrates have a same orientation within the cassette,
wherein the sensing region is selected to detect at least a side profile of each of the plurality of storage media substrates, and
wherein the controller, when in operation, determines that a first slot of the cassette contains a first carried storage media substrate of a first type of a metallic type and a substantially non-metallic type, and generates an alarm upon determining that a second slot of the cassette does not contain a second carried storage media substrate of the first type.

16. The system of claim 15, wherein determining that a second slot of the cassette does not contain a second carried storage media substrate of the first type includes one of detecting a carried storage media substrate of a second type and determining an absence of a carried storage media substrate from the second slot.

17. A non-transitory computer-readable medium containing a program which, when executed, performs an operation for determining a material type of at least one storage media substrate, the operation comprising:
using a first sensor, detecting an object that indicates the presence of at the at least one storage media substrate; and
using an inductive sensor, determining whether the at least one storage media substrate is of a metallic type.

18. The computer-readable medium of claim 17, wherein the detected object is a storage media substrate.

19. The computer-readable medium of claim 17, wherein the detected object is a cassette carrying one or more storage media substrates, and wherein the first sensor is a photoelectric sensor, and wherein the operation further comprises moving the cassette into a light beam of the photoelectric sensor.

20. The computer-readable medium of claim 17, wherein the material type is determined within a manufacturing process for a plurality of storage media substrates that includes the at least one storage media substrate, the operation further comprising:
depositing a material layer onto one or more surfaces of each of the plurality of storage media substrates, wherein the first sensor is unable to determine the material type of the plurality of storage media substrates;
after depositing the material layer, and using a conveyor device, moving a cassette carrying the plurality of storage media substrates through a sensing region for the first sensor and for the inductive sensor, wherein the plurality of storage media substrates have a same orientation within the cassette, wherein the cassette is moved substantially perpendicular to the sensing region, and wherein the sensing region is selected to detect at least a side profile of each of the plurality of storage media substrates;
determining that a first slot of the cassette contains a first carried storage media substrate that is of a first type of a metallic type and a substantially non-metallic type; and
generating an alarm upon determining that a second slot of the cassette does not contain a second carried storage media substrate of the first type.

21. The computer-readable medium of claim 20, wherein determining that a second slot of the cassette does not contain a second carried storage media substrate of the first type includes one of detecting a carried storage media substrate of a second type and determining an absence of a carried storage media substrate from the second slot.

* * * * *